US005849196A

United States Patent [19]
Kochel

[11] Patent Number: 5,849,196
[45] Date of Patent: Dec. 15, 1998

[54] COMPOSITION CONTAINING PEPTIDES AND NUCLEIC ACIDS AND METHODS OF MAKING SAME

[75] Inventor: Bonawentura Kochel, Wroclaw, Poland

[73] Assignee: Immune Modulation Maximum, New York, N.Y.

[21] Appl. No.: 726,650

[22] Filed: Oct. 7, 1996

[51] Int. Cl.⁶ .......................... B01D 61/24; A61K 35/14; A61K 35/20; A61K 35/72

[52] U.S. Cl. .......................... 210/651; 424/520; 424/529; 424/535; 514/2; 514/7; 514/44

[58] Field of Search .............................. 435/91.1; 514/2, 514/7, 44; 530/300, 350, 360, 363; 536/23.1; 210/651; 424/520, 529, 535

[56] References Cited

U.S. PATENT DOCUMENTS 5,539,082  7/1996  Nielsen et al. ........................ 530/300

OTHER PUBLICATIONS

Hanvey et al. "Antisense and Antigene Properties of Petide Nucleic Acids" Science 258: 1481–1485, Nov. 1992.

Nielsen et al. "Peptide Nucleic Acid (PNA). A DNA Mimic wiht a Peptide Backbone" Bioconjugate Chem. 5: 3–7, Feb. 1994.

Nielsen et al. "Peptide Nucleic Acids (PNAs): Potential Antisense and Anti–Gene Agents." Anti–Cancer Drug Design 8: 53–63, Aug. 1993.

"Peptide Nucleic Acids Stimulate Gamma Interferon and Inhibit the Replication of the Human Immunodeficiency Virus", by Shalom Z. Hirschman and Chey Wei Chen, in Journal of Investigative Medicine, vol. 44, No. 6, Aug. 1996, pp. 347–351.

Compilation manual for Clinical Symposium On Viral Diseases Demonstrating The Anti–Viral Biotic Properties Of The Drug Reticulose, 01 Sep. 1960, Miami, Florida.

"For The Viral Infection", informational compilation by Advanced Viral Research Corp., publication date not included.

*Primary Examiner*—George C. Elliott
*Assistant Examiner*—Thomas G. Larson
*Attorney, Agent, or Firm*—Carrier, Blackman & Associates, P.C.; Joseph P. Carrier; William F. Esser

[57] ABSTRACT

An improved composition containing peptides and nucleic acids has active components, i.e., which heighten the phagocytic activity f neutrophils, consisting of molecules with a molecular weight of at least 8 kDa, and preferably at least 15 kDa. The active components comprise peptides without aromatic portions and will absorb light at an absorption band of $\Delta\lambda=200-235$ mn, $\lambda_{max}=205$ nm, in the UV spectrum. The composition is nontoxic and is formulated using casein, blood albumin, beef peptone, nucleic acid (RNA) and a base such as sodium hydroxide. The composition stimulates phagocytic activity of neutrophils if used at sufficient concentrations. A separate composition is obtained using the same components of manufacture, but filtering or centrifuging the composition to a molecular weight of <8–15 kDa which inhibits phagocytic activity of neutrophils for application in treating auto immune diseases.

16 Claims, 3 Drawing Sheets

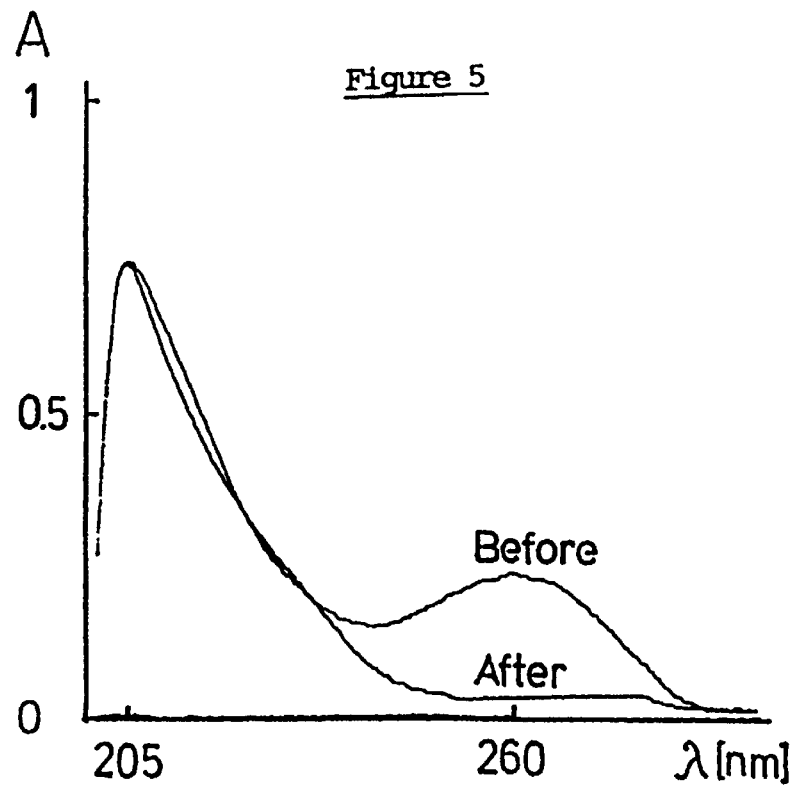
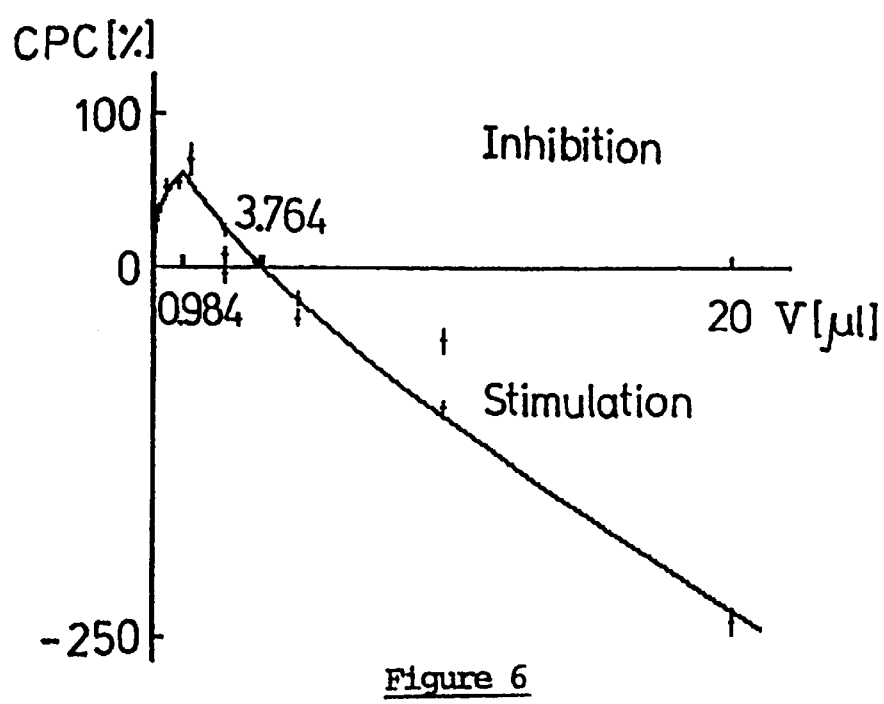

COMPOSITION CONTAINING PEPTIDES AND NUCLEIC ACIDS AND METHODS OF MAKING SAME

BACKGROUND OF THE INVENTION

1. Field of the Invention

The invention relates to a novel composition containing peptides and nucleic acid which is useful as antiviral agent and as an agent useful in treating auto immune diseases, and to methods of formulating and utilizing same. More particularly, the invention pertains to such a composition which is modified to have an improved ability to stimulate phagocytosis in humans for treatment of viruses and the like, and to methods of formulating and utilizing same.

2. Description of Relevant Art

In the art there is at least one conventionally known composition containing peptides and nucleic acids distributed under the trademark Reticulose™, which has been used as antiviral agent for humans in relation to treatment of viral infections/diseases such as influenza, herpes, infectious mononucleosis, hepatitis A and B, and most recently HIV. The known composition is referred to as "conventional composition " hereinafter. See Anderson R. H. & Thompson R. N., *Treatment of Viral Syndromes With A Lipo-protein Nucleic Acid Formulation (Reticulose)*, VIRGINIA MED. MONTH. 84, 347–353, 1957; Wegryn S. P., Marks R. A. and Baugh J. R., *Herpes Gestations*, Am J. Obst. & Gynecol. 79,812–814, 1960; Reynolds M. R., *Generalized Vaccinia Successfully Treated With Lipoprotein-Nucleic Acid Complex (Reticulose)* Arch Pediatrics 77,421–422,1960; Medoff L. R. *Use Of A Lipoprotein-Nucleic Acid Formulation In Treatment Of Infectious Mononucleosis*, Clin. Med. 69, 1–4, 1962; Catterall R. A, *A New Treatment Of Herpes Zoster, Vaccinia And Chicken Pox*, J. Roy. Coll. Gen. Practit. 19,182–183, 1970; Friedland B., *In vitro Antiviral Activity Of A Peptide-Nucleic Acid Solution Against The Human Immonodeficiency Virus And Influenza A Virus*, J. Royal Soc. Health 111, 170–171, 1991; Hirschman S. Z. and Chen W., *Peptide Nucleic Acids Stimulate Gamma Interferon And Inhibit Replication Of Human Immunodeficiency Virus*, Proc. Biomedicine '96,, Washington D.C., U.S.A., May 3–6, 1996. Thompson R. M., *A Lipo-Protein Nucleic Acid Complex In The Treatment Of Radiation Injury*, The Military Surgeon, 110, 51–58, 1952; Strickland W. N., *Summary Of Peptide-Nucleic Acid Studies Conducted At The University of Wisconsin Biotechnology Center*, Reticulose, Commonwealth Pharmaceuticals, Trenton, 1995, pp. 19–35; Friedland, B., *In Vitro Antiviral Activity of a Pepti-Nucleic Acid Solution Against The Human Immunodeficiency Virus and Influenza Virus*, J. ROY SOC. HEALTH, V. 111, No. 5, PP170, 171, 1991; and Cohen M. *The Efficacy of a Pepti-Nucleic Acid Solution (Reticulose™) For The Treatment of Hepatitis A and Hepatitis B-A Preliminary Controlled Human Clinical Trial*, J. ROY SOC. HEALTH, V. 112, No. 6, PP. 266–270 1992.

The conventional composition, also generally referred to as nucleophosphoprotein and a lipoprotein nucleic acid solution, was originally conceived by Dr. Vincent LaPenta around 1934 and was commercially available in the U.S. for a period ending in 1962. The conventional composition is known to be formulated through a mixture of casein, beef peptone, ribonucleic acid (RNA), beef serum (blood) albumin, sodium hydroxide and distilled water which is processed through heat, pressurization and filtration to a solution that is of such a small molecular weight as to be compatible with any human blood type, as discussed further hereinbelow. Essentially, the conventional composition is a complex solution of peptides and nucleic acids in which nucleic acid fragments are associated or possibly associated with short chain peptides, and wherein the molecular weight of the active components ranges from approximately 1 to 25 kDa. Presently, the conventional composition is still manufactured according to its original formulation by Advanced Viral Research Corp., in Miami, Fla.

Although the exact nature of the antiviral activity caused by complexes of peptides and nucleic acids such as the conventional composition is unknown, it appears to act either by an ability to inhibit the viruses or by alteration of a host cell response in preventing virus multiplication, and a capacity to increase antiviral, antibody response in humans, which exerts a positive therapeutic effect in both acute and chronic infection. Also very significantly, the conventional composition has been shown to be substantially free from side effects and systemic toxicity, unlike most other antiviral agents, including AZT and beta interferon.

Although the conventional composition has certain advantageous characteristics as discussed above, its effectiveness as antiviral agent is known to be limited and erratic, especially when compared to other known antiviral agents including AZT, Ribavarin, Dideoxyadenosine (DDI) and Dideoxycytidine (DDC). It thus remains a desideratum in the art for an antiviral agent which is, like the conventional composition, substantially free of ill side effects and systemic toxicity, but which also has improved effectiveness as an antiviral agent in comparison to the conventional composition.

SUMMARY OF THE INVENTION

The present invention has been developed to fulfill the above-discussed desiratum in the art.

According to the invention there is provided a composition containing peptides and nucleic acids whose active components consist essentially of molecules having a molecular weight of at least 8 kDa. Preferably, the formulation comprises peptides without aromatic portions, and has an absorption band in the interval of $\Delta\lambda=200-235$ nm, with a maximum absorbtion at $\lambda_{max}=205$ nm. Most preferably, the formulation according to the invention will stimulate a phagocytic activity of neutrophils above a predetermined quantity of the formulation.

Applicant has determined that the conventional composition, which contains active components with a molecular weight ranging from approximately 1 to 25 kDa, exhibits a phenomenon of inhibition of neutrophil phagocytic activity in humans by different groups of active components contained therein, i.e., applicant has discovered that a concentration dependent inhibition is caused by small nucleic acid fragments associated with peptides containing aromatic amino acids (MW<8–15 kDa), working as phagocytosis inhibitors. Conversely, the stimulation is caused by heavier molecules (MW>8–15 kDa), including peptides without aromatic components, which stimulate phagocytosis. Based on such discovery, applicant has modified the conventional composition by removing therefrom those active components with the molecular weight <8–15 kDa so that the resulting or modified composition exhibits mainly stimulatory effects on the phagocytic activity of neutrophils. Specifically, applicant has discovered that the composition according to the invention function as priming factors which convert neutrophils to a status more "respondent" to external stimuli such as N-formyl-L-methionyl-L-leucyl-L-phenylalanine (FMLP).

Further, although the lower weight active components (MW<8–15 kDa) of the composition are not effective as antiviral agents, they are effective in treating auto immune diseases such as non-Hodgkins Lymphoma, adult onset Leukemia, AIDS, Lupus, Scleraderma, Epstein Barr Virus, Cytomegalovirus, Chronic Fatigue Syndrome, Candidiasis, Rheumatoid and Osteo Arthritis, etc. Thus, the active components of the conventional composition may be segregated according to molecular weight and the different resulting groups of components may be selectively used to treat different viruses and auto immune diseases accordingly.

According to another important aspect of the invention there is also provided a method of preparing a composition containing peptides and nucleic acids, comprising the steps of:

combining casein, blood albumin, beef peptone, nucleic acid and a base such as sodium hydroxide in a solution of distilled water; processing the solution under elevated temperature and elevated pressure to associate nucleic acid and peptide components of the solution; and filtering or centrifuging the processed solution to remove active components having a molecular weight of less than 8 kDa. Preferably, the filtering step will be performed in multiple stages, including an initial filtering or centrifuging stage comparable to that used in making the conventional composition, which results in a solution having active components of varying molecular weights ranging from approximately 1 to 25 kDa, and a secondary filtering or centrifuging stage in which the thus filtered solution is further filtered through a semipermeable membrane such that the resulting formulation contains active components having molecular weight exclusively in a higher range of approximately 15–25 kDa.

Again, it is preferred that the active components of the composition thus processed will include peptides having no aromatic components, and the active ingredients will absorb light in a band of $\Delta\lambda=200-235$ nm, $\lambda_{max}=205$ nm, A=0.06 in the UV spectrum.

Still further, according to another aspect of the invention there is provided a method of utilizing a composition containing peptides and nucleic acids whose active components consist essentially of molecules having a molecular weight of at least 8, and most preferably 15, kDa as antiviral agent, comprising the steps of:

(a) treating a virus infected patient with a first amount of an aqueous solution of the composition per day over a first period of days;

(b) sequentially thereafter passing a second period of days without additional patient treatment of the composition;

(c) sequentially thereafter repeating steps (a) and (b) in a cyclic pattern;

(d) sequentially thereafter treating the patient with a second amount of an aqueous solution of the composition per day over a third period of days;

(e) sequentially thereafter passing a fourth period of days without additional patient treatment of the composition; and (f) thereafter testing the patient's blood to determine a status of the virus in the patient and additionally treating the patient with the composition if necessary.

Preferably, each of steps (a) and (b) will be repeated at least twice in step (c), and the second amount applied in step (d) will be approximately half of that applied in step (a). Also preferably the treatment will be applied to a patient through injection, and the total amount of the formulation given to the patient in a day will be applied in at least two portions over a period of time.

The treatment method or protocol according to the invention is effective in treating many viruses, and is often effective in completely eradicating the virus in the patient. Where the virus has not been completely eradicated, additional treatment of the virus with the composition can be determined and tailored to the patient to the testing in step (f). The composition according to the invention has mainly stimulatory effects on the phagocytic activity of neutrophils in the human body, and with the initial larger doses provided in steps (a) and (c), the patient often promptly realizes significant relief from the viral infection.

It is an object of the present invention to provide a composition containing peptides and nucleic acids which provides a mainly stimulatory effect, and another such composition which provides a mainly inhibitory effect on phagocystic activity of neutrophils in humans, and which otherwise has substantially no toxicity or ill side effects associated therewith.

It is another object of the invention to provide a relatively simple method of preparing stable solutions of the compositions.

It is a further object of the invention to provide a protocol for treating various viruses in humans using the compositions.

It is yet another object of the invention to provide an improved composition containing peptides and nucleic acid which is tailored or modified to treat different viruses, auto immune diseases and the like.

Other objects, advantages and salient features of the invention will be apparent from the following detailed description which, in conjunction with the annexed drawings, discloses presently preferred embodiments of the invention.

$$n_r(t)=(5512\pm64)\cdot\exp[-(1336\pm7)\times10^{-5}\cdot t].$$

Figure 1:
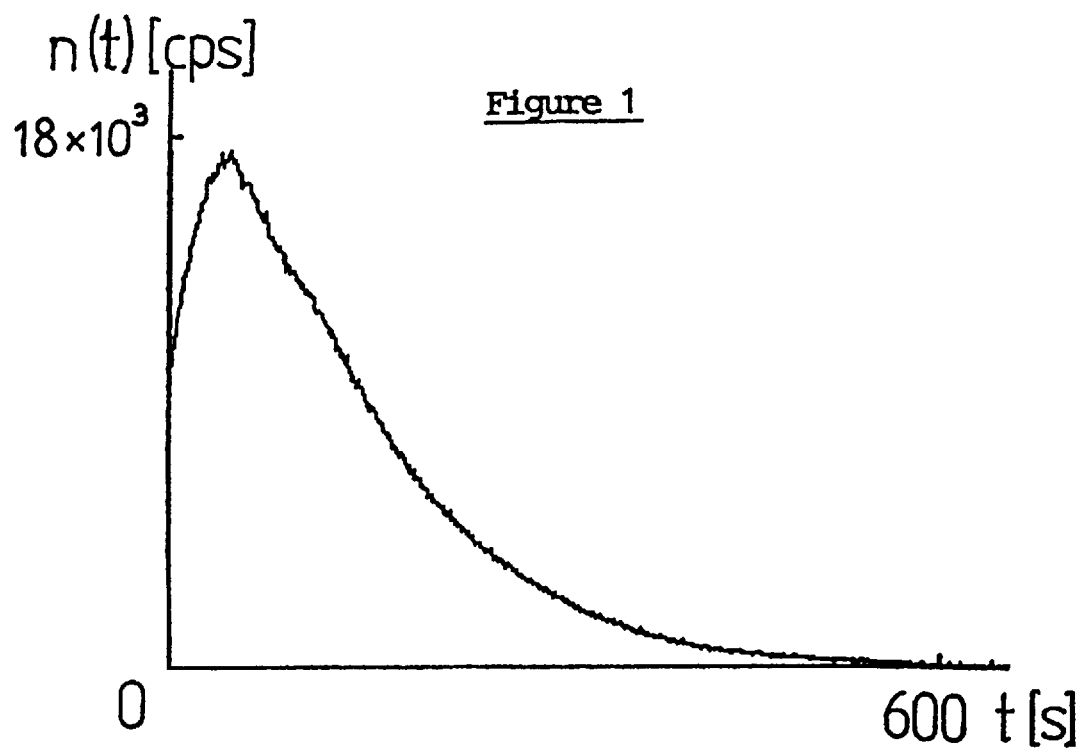
FIG. 1 is a photon-counting time series representing the time-resolved phagocyte luminescence of isolated native human neutrophils stimulated with FMLP.

FIG. 5 is an absorption spectrum in the UV range of a conventional composition and a corresponding absorption spectrum in the UV range of a composition according to the present invention.

FIG. 6 is a graph showing the volume-dependent modulatory and triggering effect of the composition according to the invention on phagocystosis demonstrated by nonmonotonic changes in the CPC (V) function.

DETAILED DESCRIPTION OF THE PREFERRED EMBODIMENTS

Preparation of the Conventional Composition

According to a known process, the known composition has been prepared over a period of days in the following manner.

First, the indicated quantities of the following components are mixed into ten liters of distilled water under slow stirring:

| RAW MATERIALS | AMOUNTS | WEIGHT PERCENTAGE |
|---|---|---|
| casein | 250 grams | 43.9% |
| blood albumin | 15 grams | 2.6% |
| beef peptone | 150 grams | 26.3% |
| nucleic acid (RNA) | 80 grams | 14.0% |
| sodium hydroxide | 75 grams | 13.2% |

After the ingredients are sufficiently dispersed in the distilled water, the solution is processed under elevated temperatures and pressure using a steam autoclave at a pressure of approximately 5–15 lbs., preferably 8–10 lbs. over a period of approximately 2–10 hours. After the heat and pressure treatment, the solution is then cooled to a temperature somewhat below room temperature and allowed to set until the following day.

The following day the solution is then filtered under an argon gas atmosphere, first through an Ertel asbestos pad filter (# 0.40 or equivalent) after which the pH of the solution is adjusted to approximately 8.5 and the solution is again filtered through a # nine (9) filter pad, after which the solution is then adjusted to pH of approximately 7.8 and again filtered through an Ertel #. EO pyrogen retention filter pad. Again, the filtered solution is refrigerated and stored until the following day. Argon gas is preferred for the gas atmosphere because it is somewhat easier to handle than other gases such as nitrogen, and because its inert nature assures sterility of the resulting composition.

On the third day, the solution is diluted to an appropriate nitrogen content and its pH adjusted to approximately 7.5, after which the solution is passed through a milipore filter HA ($0.45\mu$) for final filtration, after which it is ready for packaging and use.

The conventional composition thus formed is typically stored in sealed glass ampules under Although the example of the known process above uses specific quantities of the respective raw materials, the process may generally use raw materials in the following proportions: 40–50 weight % casein, 1–10 weight % blood albumin, 15–40 weight % beef peptone, 10–25 weight % nucleic acid, and 5–25 weight % base. an argon gas atmosphere, in appropriate quantities such as 2,5 ml and 10 ml vials.

Preparation of the Modified Composition of the Invention

The composition according to the invention is similar to the conventional composition except that it is additionally or more specifically filtered or centrifuged to remove or separate lower molecular weight active components. The composition according to the invention may be obtained by further processing the conventional composition.

According to the present invention, the conventional composition is preferably further processed by a dialysis thereof through a semi-permeable membrane having an average pore radius of approximately 10–40 Angstroms, and most preferably having an average pore radius of 24 Angstroms. Alternatively, the further processing of the conventional composition could be effected using appropriate centrifugation techniques. Appropriate semipermeable membranes or dialysis tubing may be acquired from Viskin of Serva Germany. The threshhold for molecular weight (MW) of molecules removed or separated by dialysis according to the invention is in the range of 8–15 kDa, and most preferably all molecules with a MW of <15 kDa. Applicant has discovered that the heavier active components remaining in the modified or dialyzed composition according to the invention, MW$\geq$15–25 kDa and including peptides without aromatic components, stimulate phagocytosis of the neutrophils in humans when applied above a certain quantity thereof; and that the smaller active components removed from the composition through dialysis, including small nucleic acid fragments associated with peptides containing aromatic amino acids and having molecular weights in the range of approximately 1–15 kDa, normally function as phagocytosis inhibitors at all concentrations thereof. Additionally applicant has discovered that the conventional composition exhibits a phenomenon of modulation of the neutrophil phagocytic activity caused by the interplay between the lower molecular weight components (<8–15 kDa) and the larger components ($\geq$8–15 kDa, i.e., the smaller components inhibit the stimulatory effect of the larger components. Correspondingly, in the modified composition according to the invention the smaller active components are removed so that the full stimulatory effect of the larger active components is achieved, while the smaller active components may be used in treating auto immune diseases.

Moreover, even within the range of larger, stimulating active components, applicant has been able to isolate narrower ranges of the active components which are more effective in treating different viruses, such as HIV, influenza, herpes, etc.

The much enhanced effectiveness of the composition according to the invention as an antiviral agent is understood from the following in vitro tests conducted by applicant comparing the composition according to the invention with the conventional composition. Measurements in the testing procedure were made using a single photon-counting method in order to record the time-resolved phagocyte luminescence or chemiluminescence of human isolated neutrophils. Such luminescense was first observed in 1972 and has been used since as an effective measurement of phagocytic activity and the like. Allen R. C. Stjernholm R. L., and Stele R. H., Evidence Of The Generation of (An) Electronic Excitation State(s) in Human Polymorphonuclear Lukocytes And Its Participation in Bacterial Activity, *Biochem. Biophys. Res. Commun.*, 47, 679–684, 1972. The phagocyte luminescence, a phenomenon, involves reaction of certain products of oxygen reduction generated by stimulated neutrophils or other cells. As discussed above, it is believed that the conventional composition and the modified composition according to the invention enhance the leukocytic response, increase antibody production and stimulate phagocytosis of human neutrophils, and the inventor sought to verify this thesis of phagocytic function of neurophils by means of a single photon-counting technique applied to a time-resolved phagocytic luminescence of isolated human neutrophils incubated with the composition and then stimulated with FMLP. Applicant's testing, as described fully below, not only verifies the thesis, but shows that the composition according to the invention functions as a potent stimulator of phagocytosis in human neutrophils.

Material and Method

Experimental material consisted of human neutrophils obtained from venous blood of fifteen adult healthy subjects, then isolated according to Böyum's method. See Böyum A; Isolation of Lymphocites, Granulocytes and Macrophages, *Scand. J Immnunol.* 5 (Supp 5), 9–15, 1976. The cells were counted in a Bürker's chamber and their types were determined by a Pappenheim staining procedure. The cell samples contain over 90 percent mature neutrophils, their viability evaluated by a trypan blue (1% solution in 0.15M NaCl) exceeded 95 percent.

A standard buffer solution (SBS), commonly used in chemiluminescent research was composed of phosphate buffered saline (pH 7.4), 10mM glucose and 10 mM N-[2-hydroxyethyl]piperazine-N'-[2-ethanesulfonic acid] available from Calbiochemin Switzerland.

The cell samples contain $3 \times 10^5$ neutrophils in 3 ml of SBS, were incubated at 37° C. for a period of 5 minutes with 5 microliters of the conventional composition or of the composition according to the invention in different concentrations. After the 5 minute incubation luminol (a 2.5 $\mu$M final concentration), available from Koch-Light Lab in England, was added to the samples. After the next 5 minutes phagocytic processes were initiated by FMLP, available from Sigma Chemical in the United States, then chemiluminescent processes were registered at a temperature of 37° C. by means of a single photon counting technique using a M12FQ51 photoamplifier.

Solutions of the composition according to the invention as used in the testing were made by dialyzing the conventional composition as discussed above, and particularly by dialyzing a 4 ml quantity of the conventional composition to one liter of physiological solution during 48 hours at 4° C., and the resulting solution again consisted essentially of active components of the compositions having a molecular weight in the range of 15–25 kDa.

Given the diluted nature of the dialyzed solution, and in order to redress the absorbance of A=0.77 in the 200–235 nm band which had been caused by a given volume (V) of the conventional composition, it was necessary to use the dialyzed solution of the invention at a volume 12 times as large as the volume (V) of conventional composition used. The larger volume of dialyzed composition was used in compiling data for FIG. 5.

The chemiluminscent processes have been recorded in form of photon-counting time series [n(t):t=1,2, . . . ,N], composed of the numbers of photoelectrons n(t) registered in consecutive time intervals $(t, t+\Delta t_c)$, with a counting time $\Delta t_c = 1$ s, separated by the same length intervals (constituting the dead time interval of recorder, $\Delta t_d = \Delta t_c$ during which no photoelectrons were registered). The quantity n(t) is proportional to the number of photons emitted by the light producing-system and submitted to the same statistics. An example of photon-counting time series (PCTS) describing the emission from native neutrophils stimulated by FMPL is shown in FIG. 1. Analogous PCTS, in respect to shape but not of the magnitude, occur for neutrophils incubated with the conventional composition or with the composition according to the invention.

RESULTS AND DISCUSSION

Effects of Conventional Composition on Phagocytosis

An integrated intensity of emission $I = \Sigma_t n(t)$ was measured in a time interval [1,N], corresponding to a whole process (composed of ascending and descending stages). Surprisingly, the measurements show that the samples of neutrophils treated with the conventional PNA formulation composition had integrated intensities ($I_p$) lower than those ($I_n$) of native or untreated neutrophils samples. In other words, a perturbation of phagocytosis, reflected by the inequality $I_p < I_n$ and corresponding to an inhibition of phagocytic activity of neutrophils, was demonstrated by the samples treated with the conventional composition.

The effect of the conventional composition on a phagocytic activity of neutropils was determined using the raio $I_p/I_n$ (again refer to the Allen article discussed above) and a perturbation coefficient $CPC = (1 - I_p/I_n) \cdot 100[\%]$, where the perturbation coefficient is normalized to 100% and directly proportional to the magnitude of perturbation or inhibition. See Kochel B., Time-Resolve Luminescence of Perturbed Biosystems: Scholastic Models and Perturbation Measures, *Experimentia*, 48, 1059–1069, 1992. The experimental results of the samples treated with a conventional Reticulose™ formulation are shown in Table 1.

TABLE 1

| Reticulose volume per the sample*) V [$\mu$l] | Ratio of the integrated intensities $I_p/I_n$ | Perturbation measure CPC ± SD(CPC)**) [%] |
|---|---|---|
| 0.063 | 0.388 | 61.2 ± 4.9 |
| 0.063 | 0.560 | 44.0 ± 4.2 |
| 0.078 | 0.567 | 43.3 ± 4.0 |
| 0.083 | 0.466 | 53.4 ± 3.7 |
| 0.100 | 0.480 | 52.0 ± 4.5 |
| 0.125 | 0.386 | 61.4 ± 4.8 |
| 0.156 | 0.695 | 30.5 ± 3.8 |
| 0.167 | 0.734 | 26.6 ± 4.2 |
| 0.167 | 0.664 | 33.6 ± 3.3 |
| 0.200 | 0.426 | 57.4 ± 4.0 |
| 0.250 | 0.422 | 57.8 ± 4.6 |
| 0.250 | 0.401 | 59.9 ± 4.7 |
| 0.313 | 0.337 | 66.3 ± 4.1 |
| 0.500 | 0.402 | 59.8 ± 3.6 |
| 0.500 | 0.329 | 67.1 ± 3.6 |
| 0.625 | 0.188 | 81.2 ± 3.9 |
| 1.000 | 0.248 | 75.2 ± 4.1 |
| 1.000 | 0.223 | 77.7 ± 3.4 |
| 1.250 | 0.253 | 74.7 ± 4.3 |
| 1.250 | 0.228 | 77.2 ± 3.7 |
| 1.250 | 0.224 | 77.6 ± 4.5 |
| 2.500 | 0.113 | 88.7 ± 3.8 |
| 5.000 | 0.128 | 87.2 ± 4.4 |

*)Sample volume: 3 ml.
**) $SD(CPC) = 10^4 \cdot N/I_n \cdot [1 + (I_p/I_n)^2]^{1/2}$ at $SD(n(t)) = 100$ cps.

Figure 2:
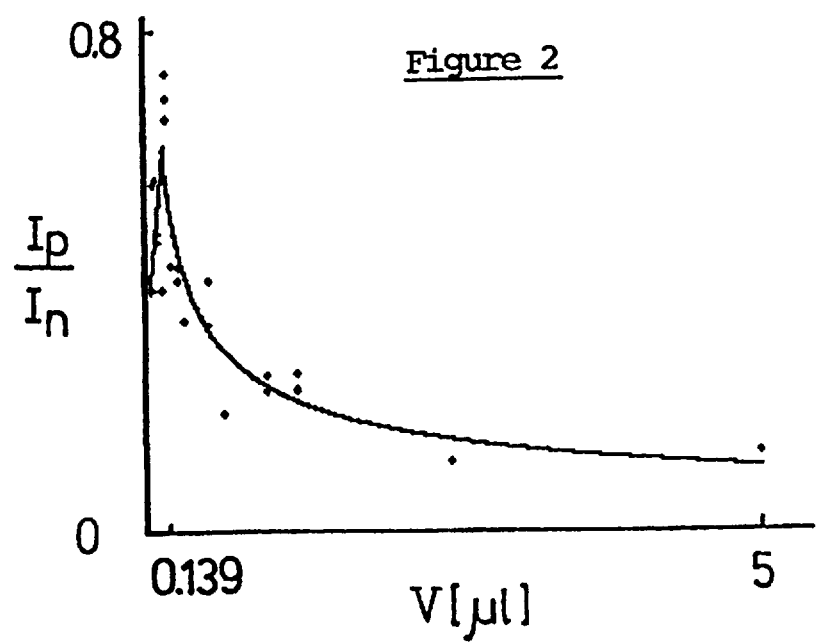
FIG. 2 is a graph depicting a nonmonotonic dependence of the $I_p/I_n$ ratio, employed as a phagocytosis perturbation measure, on the volume (V) of a conventional solution of a composition containing peptides and nucleic acids, where $I_n$ refers to native (i.e., unperturbed) neutrophils, $I_p$ refers to perturbed neutrophils, and I describes the so-called integrated luminescence.

The volume V of the conventional composition has been used as a control variable for the experiment, and a corresponding concentration of the composition in each sample (3ml) is expressed by the formula c[volume percentage]=V [$\mu$l ]/30. In the interval [0.063, 0.139] $\mu$l a linear regression of the ratio $I_p/I_n$ on V, $$I_p/I_n = (2.04 \pm 0.82) \cdot V + 0.32 \pm 0.10) \tag{1}$$

is the best one (r=0.69±0.18) amongst other elementary regressions such as power (r=0.59±0.22), logarithmic (r=0.63±0.20) or exponential (r=0.64±0.20). Refer to FIG. 2. for the linear regression.

From Eq.1 and the definition of CPC above, the following dependence of CPC on V results:

$$CPC = \{1 - [(2.04 \pm 0.82) \cdot V + (0.32 \pm 0.10)]\} \cdot 100 \tag{2}$$

The coefficients in all the regression equations are expressed together with their standard deviations (SD).

At the volumes V>0.139 µl a power regression of $I_p/I_n$ on V (Table I, FIG. 2), $$I_p/I_n(V)=(0.23\pm0.02)\cdot V^{-(0.49\pm0.05)} \qquad (3)$$

fits better (r=0.93±0.04) the experimental data points than logarithmic (r=0.87±0.06) or exponential (r=0.76±0.11) ones. Therefore a CPC (V) function takes the form:

$$CPC(V)=[1-(0.23\pm0.02)\cdot V^{-(0.49\pm0.05)}]\cdot 100. \qquad (4)$$

Figure 3:
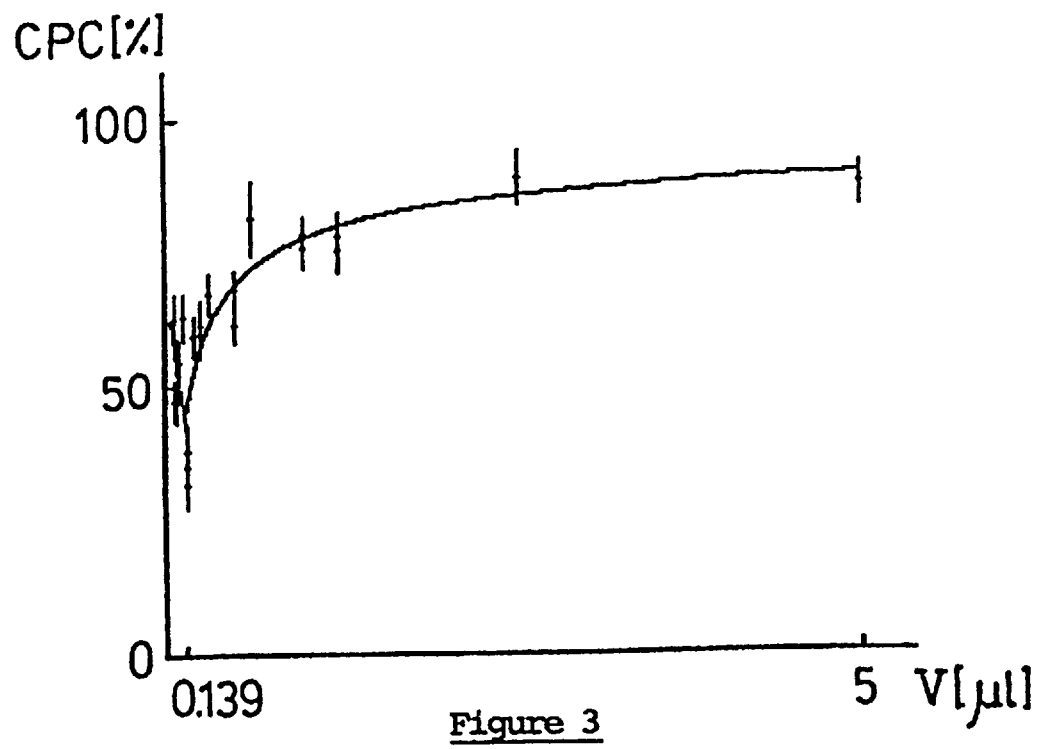
FIG. 3 is a graph showing nonmonotonic changes in the classical perturbation coefficient (CPC) describing the inhibitory effect of the conventional compositions on the phagocyctic activity of isolated human neutrophils.

From Eqs. 2 and 4 it can be seen that an inhibitory effect of the conventional composition on a phagocytic activity of neutrophils decreases when the conventional composition volume V tends from 0.063–0.139 µl then the inhibitory effect increases with V at V≧0.139 µl as shown in FIG. 3.

The results obtained using the conventional composition indicate an inhibition of phagocytosis in the entire volume range tested. Nonmontonic changes, similar to those induced by the conventional composition in the inhibition of phagocytosis, observed in the CPC=CPC(V) function (FIG. 3), are also known, although unexplained, in chemiluminescence of neutrophils in the presence of plasma. Faden H., Luminol-Dependent Whole Blood Chemiluminescence Assay, *Cellular Chemiluminescence*, V. 11 K. Van Dyke and V. Castranova (Eds.), CRC Press Boca Raton 1987, pp 183–191.

Figure 4:
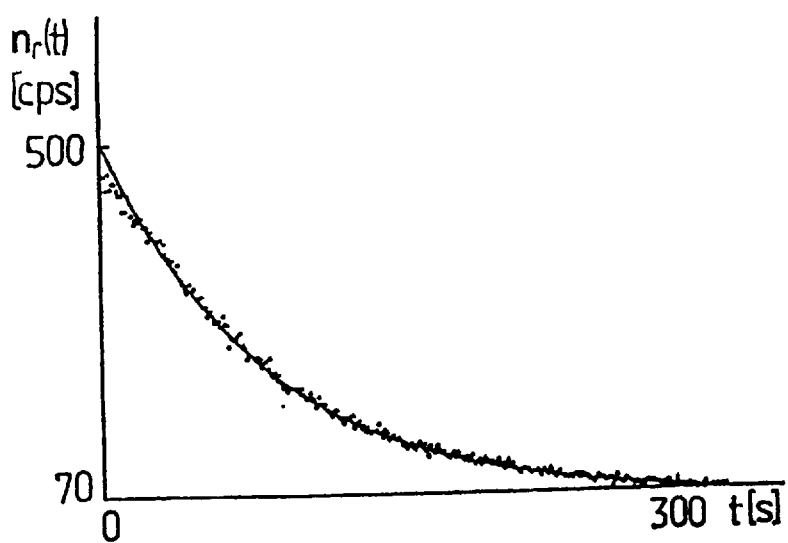
FIG. 4 is a different photon-counting times series $\{n_r(t)\}$ showing the effects on neutrophil phagocytosis induced by a given volume of the conventional composition, in which the descending stage of the $\{n_r(t)\}$ process is described as an exponential decay.

Additionally, it should be noted that the inhibitory effect of the conventional composition and the neutrophil phagocytosis does not depend on the order of addition of the convention composition and FMLP (activator). This means that the inhibition is neither caused by the receptor-ligand interaction nor by the signal transduction to the cell. This fact and a good fitting (r=0.997±0.001) shown in FIG. 4 of the $[n_r(t)]$ series by an exponential regression, $$n_r(t)=(5512\pm64)\cdot\exp[-(1336\pm7)\times10^{-5}\cdot t], \qquad (5)$$

where $\{n_r(t)\}$ is a difference series resulting from the $\{n_n(t)\}$ series (the phagocyte luminescence of native neutrophils) by substracting the $\{n_p(t)\}$ series (the phagocyte luminescence of neutrophils perturbed with 0.25 µl of the conventional composition) appear to support a possibility of scavenging of oxygen radicals by peptide nucleic acids. At k=1336 and $\Delta t_c = \Delta t_d = 1$ s the solution in Eq. 5 corresponds to a first-order ($\alpha=1$) reaction with the rate constant $k_r = k \cdot \Delta t_c^{\alpha-1} \cdot 2^{-\alpha} = 668$ photocount/s.

By comparing the results obtained for these samples using the conventional composition with those discussed below obtained using the improved composition according to the present invention, one can conclude that the inhibition obtained using the conventional composition is caused by low-molecular weight formulations (MW<8–15kDa) absorbing at 235–300 nm in the UV spectrum. These compositions have already been identified as nucleic acid fragments and/or nucleic acids associated with peptides. W. N. Strickland, Summary of Peptide Nucleic Acid Studies conducted at the University of Wisconsin Biotechnology Center, *Reticulose, Commonwealth Pharmaceuticals, Trenton*, 1995, pp. 19–35. One possible explanation of the inhibition can be based on the influence of these "small" molecules on the final stage of phagocytosis, i.e., they can play a role of scavengers of oxygen radicals. Such a phenomenon is known for, e.g., plasma where endogenous inhibitors of oxygen radicals quench luminescence. See the section by H. Faden in Cellular Chemiluminscent discussed above. Another alternative, and not necessarily disjunctive, explanation can be related to the influence of the conventional composition on the early stages of phagocytosis, e.g., the receptor expression, certain metabolic pathways, etc.

Effects of the Improved Composition of the Invention on Phagocytosis

As discussed above, the improved composition according to the invention contains active components/molecules with molecular weight greater than 8–15 kDa, preferably in a range of 15–25 kDa, and which are characterized by an absorption band ($\Delta\lambda=200-235$ nm, $\lambda^{max}=205$ nm, A=0.06) in the UV spectrum as shown in FIG. 5. By comparison, a sample of the conventional composition at the same absorption band (200–235nm) has an absorption of A=0.77. In order to redress such absorbance of the conventional composition in the samples involving the improved composition according to the invention, it is necessary to use the improved composition in a volume of $V_D=12\cdot V$, where V is a given volume of the conventional composition. Results of the tests involving the improved composition according to the invention are set forth in Table 2 below.

TABLE 2

| Equivalent Reticulose volume *) per the sample **) V [µl] | Ratio of the integrated intensities $I_p/I_n$ | Perturbation measure CPC ± SD(CPC) [%] | Remarks |
|---|---|---|---|
| 0.167 | 0.648 | 35.2 ± 5.3 | Inhibition |
| 0.420 | 0.476 | 52.4 ± 4.4 | of phagocytic |
| 0.830 | 0.452 | 54.8 ± 2.4 | activity of |
| 0.830 | 0.436 | 56.4 ± 3.7 | neutrophils |
| 1.250 | 0.292 | 70.8 ± 9.7 | |
| 2.500 | 0.751 | 24.9 ± 3.7 | |
| 2.500 | 0.925 | 7.5 ± 4.5 | |
| 2.500 | 1.051 | −5.1 ± 4.7 | Stimulation |
| 5.000 | 1.220 | −22.0 ± 4.6 | of phagocytic |
| 5.000 | 1.359 | −35.9 ± 4.8 | activity of |
| 10.000 | 1.512 | −51.2 ± 8.3 | neutrophils |
| 10.000 | 1.974 | −97.4 ± 4.4 | |
| 20.000 | 3.454 | −254.4 ± 9.2 | |

*) A given volume ($V_D$) of the Reticulose dialysate has been expressed by the equivalent volume of Reticulose (V) causing the same absorbance at 205 nm.
**) Sample volume; 3 ml.

Generally speaking, CPC>0 at $I_p<I_n$, whereas if $I_p>I_n$ then CPC<0 and therefore a quantity $CPC_+$ defined by the equation $CPC_+=(I_p/I_n-1)\cdot 100$ describes a stimulation of phagocytosis in percentages.

With reference to Table 2, in the volume interval [0.167, 0.984]µl interval the changes in the $I_p/I_n$ or CPC values (as shown in FIG. 6), caused by changes in V (cf.Table 2) are expressed by regressions:

$$I_p/I_n(V)=1-(0.063\pm(0.03)\cdot V^{(0.31\pm0.06)}, \qquad (6)$$

$$CPC(V)=(62.6\pm2.0)\cdot V^{(0.31\pm0.06)}, \qquad (7)$$

at a correlation coefficient r=0.96±0.04. Therefore, in the discussed volume interval the inhibition of phagocytosis, caused by the improved composition of the invention, increases with the volume of the formulation used.

According to equations 4 and 7 the inhibition caused by the conventional composition at V=[0.167, 0.984] µl is higher than that by the composition of the invention by 8.8–17.2 percentage points. This means that the redress of the concentration of active components in the composition of the invention, which absorb in the 200–235 nm interval, is not sufficient for redressing the perturbation of phagocytosis to the level caused by conventional composition. Such 8.8–17.2 percentage point decrease in the perturbation is directly related to the absence of those smaller molecular weight formulations (MW<8–15 kDa) which were removed or dialyzed away according to the invention. Since those smaller molecular weight formulations have an absorption band at 235–300 nm one can conclude that they are nucleic acids and/or their associations with peptides, and state that their contribution to the inhibition of phagocytosis ranges from 8.8 to 17.2%. Consequently the higher molecular weight formulations (MW >8–15 kDa) occuring in the composition according to the invention show an 82.8–91.2 percent contribution to the inhibition phagocytosis in the [0.167, 0.984] μl range.

In a higher range [0.984, 3.764] μl interval the changes in $I_p/I_n$ or CPC (FIG. 6), caused by changes in V (cf. Table 2), are expressed by the regressions:

$$I_p/I_n(V)=(0.38\pm0.07)\cdot V^{(0.73\pm0.11)} \quad (8)$$

$$CPC(V)=[1-(0.38\pm0.07)\cdot V^{(0.73\pm0.11)}]\cdot 100, \quad (9)$$

at a correlation coefficient r=0.94±0.04. There occurs an inhibition of phagocytosis caused by the composition of the invention at V=[0.984,3.764] μl and a stimulation at V>3.764 μl because CPC(3.764)=0.

The composition, according to the invention, inhibits a phagocytosis at V=[0.984,3.764] μl, although the inhibition decreases to zero, according to Eq. 9, when V increases to 3.764 μl. In comparison with the inhibition caused by the conventional composition, there is discerned a difference ranging from 14.4 to 88.0 percentage points. For instance, 3.764, μl of the composition of the invention does not inhibit a phagocytosis (CPC=0) whereas the same volume of the conventional composition inhibits phagocytosis to 88.0 percentage points. Again, complexes of peptides and nucleic acids appear to be responsible for that inhibition.

The difference between the composition of the invention in comparison to the conventional composition are particularly noticeable at volumes greater than 3.764 μl because the formulation of the invention stimulates a phagocytosis at such volumes, as represented by negative values of CPC in Eq. 8 above, whereas the conventional composition continues to inhibit the phagocytosis as reflected by the sample volume of 5.000 μl in Table 1 above showing that the conventional formulation inhibited phagocytosis at 87.2 percentage points.

Whereas negative values of CPC in Eq. 8 above indicate stimulation of phagocytosis, positive values of the CPC (V) function in Eq. 10 below corrrespondingly indicate stimulation of phagocytosis.

$$CPC_+(V)=[(0.38\pm0.07)\cdot V^{(0.73\pm0.11)}-1]\cdot 100 \quad (10)$$

It should be emphasized that the composition according to the invention did not change the phagocytic activity of neutrophils (CPC=0) after the neutrophils have been stimulated by FMLP, i.e., the changes in the phagocytic activity were observed only when neutrophils have been treated by the composition prior to the stimulation by FMLP. For instance, the 245% stimulaton of phagocytosis occuring at V=20,μl was possible only when the incubation with the composition preceded the addition of FMLP. This fact indicates the phenomenon of priming. Downey G. P., Fukushima T., Fialkow L. and Waddell T. K., Intracellular Signalling In Neutrophil Priming and Activation, *Sem. In Cell Biol.,* 6, 345–356, 1995. The priming is caused by the active components in the composition with MW>8–15 kDa, because that phenomenon does not occur for the conventional Reticulose™formulation where it is blocked by the low molecular-weight active components (MW <8–15 kDa), i.e., nucleic acid fragments and their associations with peptides.

Amongst the possible pathways by which the formulations contained in the composition of the invention affect neutrophil phagocytosis, the following are most likely: the influence on a receptor expression; binding of a stimulus (FMLP) with receptors; transduction of a signal to the cell interior; and the activation of NADPH-oxidase. The above-mentioned and other forms of influence on metabollic pathways result in some changes in the production of active forms of oxygen (e.g., $'O_1,O_2^-$) which in turn determine the final stage of phagocytosis.

Conclusions

As understood from the foregoing test results, the conventional PNA formulation inhibits a phagocytic activity of neutrophils for all of the investigated volumes. The inhibition decreases linearly (CPC(V)=2.04·V+0.32) in the [0.063, 0.139] μl interval, then increases nonlinearly ($CPC(V)=[1-0.23\cdot V^{-0.49}]\cdot 100$) at V>0.139 μl with the conventional composition used. The inhibitory effect of the conventional composition on phagocytosis of neutrophils is caused by nucleic acid fragments (possibly associated with peptides) having a low molecular weight, i.e., MW<8–15 kDa, whereas the composition according to the invention with active components having MW >8–15 kDa stimulate phagocytosis.

Specifically, the composition of the invention inhibits a phagocytic function of isolated human neutrophils at low volumes (<3.674 μl) of the diluted solution used. The inhibition of phagocytosis increases according to a power low ($CPC(V)-62.6\cdot V^{0.31}$) for volumes below 0.984 μl and then decreases nonlinearly ($CPC(V)=[1-0.38\cdot V^{0.73}]\cdot 100$) for V>0.984 μl. At the volume threshold of 3.764 μl it causes no inhibition of a phagocytic function of neutrophils, and above such volume threshold it stimulates such phagocytic function. The stimulation changes with the composition volume according to a power low ($CPC_+(V)=[0.38\cdot V^{0.73}-1]\cdot 100$). Reactive components of the composition according to the invention (peptides without aromatic components) characterized by MW>8–15 kDa and absorption at 200–235 nm, play a role of priming factors, which convert neutrophils to a status more "respondent" to external stimuli such as FMLP.

The presence of peptide nucleic acids with MW<8–15 kDa (as it holds for the conventional composition) annihilates the stimulation of phagocytosis by the heavier (MW>8–15 kDa) active components. On the other hand, the compositions according to the invention, having mainly stimulatory effects on a phagocytic activity of neutrophils, are obtained by separating away the small components (MW<8–15 kDa) by a dialysis or centrifuge of the conventional composition through an appropriate semipermeable membrane, such as a 24 Angstrom membrane or through appropriate centrifugation. Further, the removed or separated lower weight active components (MW<8–15 kDa) can be used in treating auto immune diseases as discussed above. Basically, the lower weight active components of the composition function to slow down the degeneration caused by the auto immune diseases. Moreover, the composition according to the invention can be tailored to treat different viruses by further narrowing a range of molecular weights of the active components contained therein.

Use of the Composition of the Invention

The compositions of the present invention are most preferably administered by way of injectable aqueous solutions or preparations, discussed further hereinbelow in relation to specific examples of uses, but may be otherwise administered orally, parenterally, sublinguilly, by inhalation spray, rectally, or topically in dosage unit formulations containing appropriate non-toxic carriers, adjuvants and vehicles as desired. The term parenteral encompasses subquetaneous injections, intravenous, intramuscular, intraternal injection or infusion techniques.

As an injectable aqueous solution, the composition according to the invention may be packaged in appropriate sized glass ampules similar to manner in which the conventional composition is packaged as discussed above, or in appropriate larger stoppered vials.

According to the invention, different protocols have been developed for treating different viral infections with the compositions of the invention. Below are presented four protocols for treating herpes/genital warts; Hepatitis B; Hepatitis C, Chronic Fatigue, Epstein-Barr; and HIV using injectable aqueous solutions of the compositions of the invention. According to an important aspect of the invention, as discussed above, the composition may be modified or specifically adapted for treating different viruses.

Protocol No. 1

Have test performed for Herpes A,B and C, include IGG, IGA.

Inject composition solution twice daily for three (3) days—1 mL each injection.

Take no medication for seven (7) days.

Inject composition Solution twice daily for three (3) days—1 mL each injection.

Take no medication for seven (7) days.

Inject composition solution twice daily for three (3) days—1 mL each injection.

Wait 14 days.

Have Herpes test performed for specific Herpes type established in original Herpes panel (have both IGG and IGA performed).

The composition solution may initially be refrigerated, though it need not be. If so, bring the syringe to body temperature before injection (e.g. holding it in hand). Inject slowly to provide painless infusion. If there is pain at injection site because of cold composition or too fast injection, pain will dissipate within 15 minutes. Rotate injection sites. NOTE: 60% Of Herpes patients clear infection using this protocol. The remaining 40% are persons that have a weakened immune system because of stress or other causes such as sunburn. For these patients, it is recommended to provide a maintenance dosage of ½ mL twice a day for one day per month to prevent recurrence.

Protocol No. 2

Hepatitis B

Have test performed for Hepatitis B include IGG, IGA.

Inject composition solution—1 mL two times daily for 7 days. Next 7 days—nothing.

Inject composition solution—1 mL two times daily for 7 days. Next 7 days—nothing.

Inject composition solution—1 mL two times daily for 7 days. Next 7 days—nothing.

Inject composition solution—½ mL two times daily for 7 days. Next 7 days—nothing.

Inject composition solution—½ mL two times daily for 7 days. Next 7 days—nothing.

Do respective blood work 2 months after protocol has been completed, and adjust per attending physician's recommendation.

Rotate injection sites.

Hepatitis C. Chronic Fatigue Epstein-Barr

Inject composition solution—1 mL two times daily for 7 days. Next 7 days—nothing.

Inject composition solution—1 mL two times daily for 7 days. Next 7 days—nothing.

Inject composition solution—1 mL two times daily for 7 days. Next 7 days—nothing.

Inject composition solution—½ mL two times daily for 7 days. Next 7 days—nothing.

Inject composition solution—½ mL two times daily for 7 days. Next 7 days—nothing.

Do respective blood work after protocol has been completed, and adjust per attending physician's recommendation.

Vitamin C I.V. should be given in conjunction with subcutaneous medication for a minimum of 28 days.

| | |
|---|---|
| 20 grams Ascorbic Acid | 10 mL Calcium Gluconate |
| 6 mL Magnesium Chloride | 1 mL B-Composition |
| 1 mL B-12 | 1 mL B-6 |
| Adjust pH to 7.4 with Sodium Bicardonate | |

Put above ingredients in 500 mL sterile distilled water and run for 3 hours daily for no less than 28 days. After each 7 days add additional 10 grams of Ascorbic Acid to a maximum of 50 grams Ascorbic Acid in the last week of Vitamin C I.V., treatments as long as patient can tolerate additional Vitamin C. If patient develops diarrhea or upset stomach back off Vitamin C (Ascorbic Acid to previous tolerable level).

Protocol No. 4 HIV

Inject composition solution—1 mL two times daily for 7 days. Next 7 days—nothing.

Inject composition solution—1 mL two times daily for 7 days. Next 7 days—nothing.

Inject composition solution—1 mL two times daily for 7 days. Next 7 days—nothing.

Inject composition solution—½ mL two times daily for 7 days. Next 7 days—nothing.

Do respective blood work including P-24 antigen test 2 months after protocol has been completed, and adjust per attending physician's recommendation.

Rotate injection sites.

These four exemplary protocols according to the invention reflect the effectiveness of the improved composition in treating many viruses, and auto immune diseases and often are effective in completely eradicating the virus or disease in the patient. Where the virus or disease is not completely eradicated, additional treatment of the virus with the composition according to the invention can be determined and tailored to the patient through testing of the patient after administration of the protocol program. With the initial larger doses provided in the early steps according to the protocols of the invention, patients often promptly realize significant relief from the viruses and diseases.

Although there have been described above what are considered to be presently preferred embodiments of the invention, it will be understood as various changes and modifications may be made thereto without departing from the spirit or essence of the invention. The scope of the invention is indicated by the appended claims, rather than by the foregoing description.

I claim:

1. In a composition containing peptides and nucleic acids, with components having molecular weights in a range from about 1–25 kDa and which absorbs light in at least two bands having maximum values at 205 nm and 260 nm, and wherein the composition is initially formulated by processing a mixture of casein, blood albumin, beef peptone, nucleic acid, and a base in an appropriate medium at an elevated temperature and an elevated pressure, and separating therefrom components having molecular weights outside of the range from about 1–25 kDa, the improvement comprising:

processing said composition to remove therefrom components having molecular weights of <8 kDa such that the processed composition absorbs light in a wavelength interval from about 200–235 nm with a maximum absorbance at 205 nm.

2. The composition according to claim 1, wherein said composition is processed by dialyzing the composition through a membrane having an average pore size of 10–40 Angstroms.

3. The composition according to claim 1, wherein said mixture contains 40–50 weight % casein, 1–10 weight % blood albumin, 1–3 weight % beef peptone, 10–25 weight % nucleic acid, and 5–25 weight % base.

4. The composition according to claim 1, wherein said mixture contains 43.9 weight % casein, 2.6 weight % blood albumin, 26.3 weight % beef peptone, 14.0 weight % nucleic acid, and 13.2 weight % sodium hydroxide.

5. In a composition containing peptides and nucleic acids, with components having molecular weights in a range from about 1–25 kDa and which absorbs light in at least two bands having maximum values at 205 nm and 260 nm, and wherein the composition is initially formulated by processing a mixture of casein, blood albumin, beef peptone, nucleic acid, and a base in an appropriate medium at an elevated temperature and an elevated pressure, and separating therefrom components having molecular weights outside of the range from about 1–25 kDa, the improvement comprising:

processing said composition to remove therefrom components having molecular weights of $\geq$8 kDa such that the processed composition absorbs light in a wavelength interval from about 235–300 nm.

6. The composition according to claim 5, wherein said composition is processed by dialyzing the composition through a membrane having an average pore size of 10–40 Angstroms.

7. The composition according to claim 5, wherein said mixture contains 40–50 weight % casein, 1–10 weight % blood albumin, 1–3 weight % beef peptone, 10–25 weight % nucleic acid, and 5–25 weight % base.

8. The composition according to claim 5, wherein said mixture contains 43.9 weight % casein, 2.6 weight % blood albumin, 26.3 weight % beef peptone, 14.0 weight % nucleic acid, and 13.2 weight % sodium hydroxide.

9. In a method of preparing a composition containing peptides and nucleic acids comprising the steps of:

forming a mixture of casein, blood albumin, beef peptone, nucleic acid and a base in an appropriate medium;

processing the mixture at an elevated temperature and an elevated pressure;

separating from the processed mixture components having molecular weights outside of a range from about 1–25 kDa such that the mixture absorbs light in at least two bands having maximum values at 205 nm and 260 nm;

the improvement comprising the step of:

further removing from the mixture components having molecular weights of <8 kDa such that the mixture absorbs light in a wavelength interval from about 200–240 nm with a maximum absorbance at 205 nm.

10. The method according to claim 9, wherein said further separating step involves dialyzing the mixture through a membrane having an average pore size of 10–40 Angstroms.

11. The method according to claim 9, wherein said mixture contains 40–50 weight % casein, 1–10 weight % blood albumin, 1–3 weight % beef peptone, 10–25 weight % nucleic acid, and 5–25 weight % base.

12. The method according to claim 9, wherein said mixture contains 43.9 weight % casein, 2.6 weight % blood albumin, 26.3 weight % beef peptone, 14.0 weight % nucleic acid, and 13.2 weight % sodium hydroxide.

13. In a method of preparing a composition containing peptides and nucleic acids comprising the steps of:

forming a mixture of casein, blood albumin, beef peptone, nucleic acid and a base in an appropriate medium;

processing the mixture at an elevated temperature and an elevated pressure;

separating from the processed mixture components having molecular weights outside of a range from about 1–25 kDa such that the mixture absorbs light in at least two bands having maximum values at 205 nm and 260 nm;

the improvement comprising the step of:

further removing from the mixture components having molecular weights of >8 kDa such that the mixture absorbs light in a wavelength interval from about 235–300 nm.

14. The method according to claim 13, wherein said further separating step involves dialyzing the mixture through a membrane having an average pore size of 10–40 Angstroms.

15. The method according to claim 13, wherein said mixture contains 40–50 weight % casein, 1–10 weight % blood albumin, 1–3 weight % beef peptone, 10–25 weight % nucleic acid, and 5–25 weight % base.

16. The method according to claim 13, wherein said mixture contains 43.9 weight % casein, 2.6 weight % blood albumin, 26.3 weight % beef peptone, 14.0 weight %.

* * * * *